United States Patent [19]

McKinney

[11] Patent Number: 5,395,974

[45] Date of Patent: * Mar. 7, 1995

[54] LEWIS ACID CATALYZED AMMONOLYSIS OF NYLON

[75] Inventor: Ronald J. McKinney, Wilmington, Del.

[73] Assignee: E. I. Du Pont de Nemours and Company, Wilmington, Del.

[ * ] Notice: The portion of the term of this patent subsequent to Apr. 12, 2011 has been disclaimed.

[21] Appl. No.: 184,335

[22] Filed: Jan. 21, 1994

[51] Int. Cl.$^6$ ............................................. C07C 209/62
[52] U.S. Cl. .................................... 564/488; 540/485; 540/538; 540/540; 558/311; 558/313; 558/318; 558/445; 558/452; 558/454; 558/456; 562/590; 562/593; 564/198; 564/498; 564/511
[58] Field of Search ................ 564/488, 198, 498, 511; 540/485, 538, 540; 558/311, 313, 318, 445, 452, 454, 456; 562/590, 593

[56] References Cited

U.S. PATENT DOCUMENTS

| | | | |
|---|---|---|---|
| 2,343,174 | 8/1940 | Edison et al. | 260/78 |
| 3,182,055 | 2/1963 | Bonfield et al. | 260/239.3 |
| 3,668,109 | 6/1972 | Kiovsky et al. | 208/10 |
| 3,750,600 | 8/1973 | Ohsol et al. | 110/343 |
| 4,085,130 | 1/1974 | Cobb | 260/465.2 |
| 4,720,328 | 9/1983 | Corbin et al. | 203/37 |
| 4,973,746 | 10/1988 | Blackmon et al. | 562/442 |

FOREIGN PATENT DOCUMENTS

| | | |
|---|---|---|
| 715592 | 2/1964 | Canada . |
| 739505 | 2/1964 | Canada . |
| 53-28893 | 8/1978 | Japan . |
| 54-84525 | 7/1979 | Japan . |
| 1172997 | 7/1966 | United Kingdom . |

OTHER PUBLICATIONS

Gimaev et al., *Chem. Abs.* 104: 170554s (1985).

*Primary Examiner*—Glennon H. Hollrah
*Assistant Examiner*—Scott C. Rand

[57] ABSTRACT

The present invention relates to a method of reacting polyamides or mixtures thereof with ammonia to obtain a mixture of monomers. The reaction is carried out in the presence of certain Lewis Acid catalyst precursors.

6 Claims, No Drawings

LEWIS ACID CATALYZED AMMONOLYSIS OF NYLON

BACKGROUND OF THE INVENTION

1. Field of the Invention

The present invention relates to a method of reacting polyamides, such as nylon 6,6 and nylon 6, with ammonia to obtain a mixture of monomers. The reaction is carried out in the presence of certain Lewis Acid catalyst precursors.

1. Description of the Related Art

Japanese Patent Application Publication 54-84,525 (1979) describes a process for the production of 6-aminocapronitrile (6ACN) and caprolactam (CL) by treating molten polycaproamide (nylon 6) at elevated temperature (340° C.) and pressure (6 kg/cm$^2$) with ammonia gas.

British Patent 1,172,997 discloses conversion of a polyamide into monomeric compounds by heating the polyamide with ammonia in the presence of hydrogen and a hydrogenation catalyst. Suitable polyamides which may be converted according to the described process include polyhexamethylene adipamide (nylon 6,6) and polycaprolactam (nylon 6). With nylon 6,6, the products obtained are hexamethylenediamine (HMD), hexamethyleneimine, and a small amount of unidentified material. When nylon 6 is reacted in accordance with the process, the resulting products are hexamethylenediamine (HMD), hexamethyleneimine, and N-(6-aminohexyl)-hexamethyleneimine.

Co-pending, co-assigned, U.S. patent application Ser. No. 07/997,612 (Ammonolysis of Nylon), the disclosure of which is hereby incorporated by reference, teaches a nylon ammonolysis process for obtaining a mixture of monomers from nylon 6,6 or a mixture of nylon 6,6 and nylon 6. Monomers obtained from the reaction can be used for reconversion into useful polyamides or for other purposes. The ammonolysis process comprises reacting nylon 6,6 or a mixture of nylon 6,6 and nylon 6, with at least 1 equivalent of ammonia per amide group of the polymer at a temperature between 250° and 400° C. and at a pressure of at least 100 psig, the ratio of nylon 6,6 to nylon 6 in said mixture being from 1:9 to 9:1 on a weight basis.

It has now been found that the ammonolysis process described in the above-mentioned patent application Ser. No. 07/997,612 can be made more efficient when the process is carried out in the presence of certain Lewis acid catalyst precursors.

SUMMARY OF THE INVENTION

The present invention provides a process for preparing a mixture of monomers comprising reacting polyamides, such as nylon 6, nylon 6,6 or a mixture thereof, with at least 1 equivalent of ammonia per amide group of the polymer at a temperature between 250° and 400° C. and at a pressure of at least 100 psig. The reaction is carried out in the presence of certain Lewis Acid catalyst precursors.

DETAILED DESCRIPTION OF THE INVENTION

In accordance with the present invention, it has been discovered that the ammonolysis of polyamides can be made more efficient by running the ammonolysis reaction in the presence of certain Lewis acid "catalyst precursors". A Lewis acid is defined as a molecule or ion which is capable of accepting an electron pair from another molecule or ion by means of coordination. By "catalyst precursor," it is meant to indicate that the Lewis acid may maintain its original structure during the ammonolysis reaction or its structure may be changed.

In general, the ammonolysis of nylon involves heating the polyamides with ammonia at elevated temperature and pressure. Suitable polyamides include aliphatic polyamides such as poly(hexamethylene adipamide) (nylon 6,6); poly(hexamethylene sebacamide) (nylon 6,10); polycaprolactam (nylon 6); and poly(decamethylene carboxamide) (nylon 11); and aromatic polyamides such as poly(m-phenylene isophthalamide) ("Nomex"). Preferably, nylon 6, nylon 6,6, or mixtures thereof, where the ratio of nylon 6,6 to nylon 6 in the mixture is in the range of 9:1 to 1:9 on a weight basis, are reacted. Sufficient ammonia is employed to provide at least 1 mole of ammonia per mole of amide groups in the nylon polymer. Preferably, an excess of ammonia is employed. The reaction is not carried out in the presence of hydrogen, and thus no hydrogenation catalyst is used. The reaction proceeds at temperatures between 250° to 400° C. It is preferred to use temperatures from 300° to 350° C. for efficient operation. The reaction rate is also pressure dependent with pressures of 100 to 5000 psig being preferred and 500 to 2500 psig being most preferred. The procedure can be performed as a batch or continuous process, the latter being much preferred. The monomer products generally include hexamethylenediamine (HMD), 5-cyanovaleramide (CVAM), and adiponitrile (AND) from nylon 6,6; and caprolactam (CL), 6-aminocaproamide (ACAM), and 6-aminocapronitrile (6ACN) from nylon 6. The identification of the monomers and the content of each monomer in the recovered monomer mixture can be determined by quantitative gas-liquid chromatography.

The reaction co-produces water which, because of the equilibrium nature of the reaction, inhibits complete conversion of the intermediately formed amides to nitriles. To further the conversion to nitriles, it is desirable to remove the water as it is formed, thereby shifting the equilibrium. This may be accomplished by passing ammonia through the reaction zone and out through a pressure letdown device, such as a backpressure regulator. In this manner, monomer products may also be removed from the reactor as they are formed and collected. Ammonia is not condensed with the monomers and passes into a subsequent chamber. An inert carrier such as nitrogen gas may be substituted for some of the excess ammonia.

The monomeric products may then be hydrogenated to hexamethylenediamine (HMD) via a separate reaction. Those monomers which are not converted to HMD may be recycled through the above-described process.

In general, it has been found that the activity of a given metal increases with increasing acidity of the conjugate acid of the anion, e.g. $M(OC_3H_7)_x[18] < M(O_2CCH_3)_x[4.7] < MCl_x[-7] < M(O_3SCF_3)_x—[-11]$ (where the pK$_a$ of the conjugate acid of the anion is given in square brackets). A definition of pKa is provided in the textbook, "Organic Chemistry" by K. Peter C. Vollhardt (W. H. Freeman & Co., N.Y., 1987) at pages 205-206:

$$pK_a = -\log K_a$$

where $K_a = [H_3O+][A-]/[HA]$ where A— is the counterion of the conjugate acid HA. Typical anions with the pKa of their conjugate acids given in square brackets are: $CF_3SO_3$—[−11], I—[−11], Br—[−8], Cl—[−7], $ArSO_3$—[−7] (Ar=aryl group), $CF_3CO_2$—[0.2], $CH_3CO_2$—[4.7], and $CH_3O$—[15.5]. The above-mentioned pKa values are provided in the textbook, "Advanced Organic Chemistry: Reactions, Mechanism, and Structure" by Jerry March (McGraw-Hill Book Co., N.Y., 1968) pages 219-221. In addition, with respect to Lewis acids of the elements listed in groups 3-10, it has been found that activity increases upon moving from right to left of the Periodic Table, i.e. Ni, Co<Fe, Mn, Cr<Ti. Because of these two properties, a counterion which may render a late transition metal element such as nickel nearly inactive, may still allow significant activity for a more active metal such as titanium. In accordance with these properties, the Lewis acids suitable for use in this invention have specific pKa values. (The following group numbers refer to those group numbers of the 1985 IUPAC proposal, and a Periodic Table with these group numbers is provided in the foregoing textbook, "Organic Chemistry.")

Suitable Lewis acid catalyst precursors for use in this invention include metal salts made from the alkaline earth elements listed in Group 2 of the Periodic Table (Beryllium, Magnesium, Calcium, Strontium, Barium, and Radium) and containing at least one anion whose conjugate acid has a $pK_a < 15$.

The Lewis acid catalyst precursors may also be a complex containing an element selected from the following elements listed in Groups 3 and 4: scandium, titanium, yttrium, and zirconium, and at least one anion whose conjugate acid has a $pK_a < 20$.

Other suitable Lewis acid catalyst precursors include complexes containing a metal selected from the metals listed in Groups 5-14, and at least one anion whose conjugate acid has a $pK_a < 4$.

Preferably, the Lewis acid is a complex containing a cation selected from the group consisting of scandium, titanium, manganese, rhenium, iron, copper, zinc, molybdenum, tungsten, and aluminum, and at least one anion selected from the group consisting of chlorine, bromine, and iodine.

More preferably, the Lewis Acid precursor is a complex selected from the group consisting of $ScX_3$ $TiX_4$, $MnX_2$, $REX_5$, $FeX_3$, $CuX_2$, $CuX$, $ZnX_2$, $MoX_6$, $WX_6$, $AlX_3$, where X=Cl, Br, or I.

The addition of certain Lewis acids to the ammonolysis reaction has been found to increase the rate of the process, thus improving the efficiency. This increase in reaction efficiency helps to make nylon recycling efforts more economically feasible.

The present invention is further described by the following examples, but these examples should not be construed as limiting the scope of the invention.

EXAMPLES

Example 1

A vertical cylindrical reactor (72 cc inner volume) with a 5 micron fritted disk at the bottom is charged with nylon 6,6 (polyhexamethylene adipamide)(7.5 g.), nylon 6 (polycaproamide) (7.5 g) and a catalyst precursor from Table 1 (0.15 g), sealed and purged with nitrogen. Liquid ammonia is fed (1.8 g/min) into the reactor through a preheater (300° C.) and the fritted disk. The reactor is heated by means of a band heater to 300° C. Constant pressure in the reactor is maintained by means of Grove back pressure regulator at 1000 psig throughout the reaction period (30 minutes). Monomeric products are volatilized under reaction conditions and carried from the reactor, through the Grove regulator and condensed out of the ammonia stream in a cool receiver. The ammonia passes out of the receiver into a water scrubber. The monomeric products in the receiver are analyzed by quantitative gas-liquid chromatography for hexamethylenediamine (HMD), 6-aminocapronitrile (6ACN), adiponitrile (AND), caprolactam (CL), 6-aminocaproamide (ACAM), and 5-cyanovaleramide (CVAM) to give a total yield of useful monomers, calculated by the following formula:

Yield = 100x([6ACN]+[CL]+[ACAM]+[HMD]+[AND]+[CVAM]/[nylon]

where square brackets indicate moles and

[nylon]=(gm nylon 6+gm nylon 6,6)/113=0.133 moles.

TABLE 1

| *pKa of HA | Catalyst Precursor | mmoles catalyst | monomers (mmoles) | | | | | | total monomers YIELD (%) |
|---|---|---|---|---|---|---|---|---|---|
| | | | HMD | 6ACN | ADN | CL | ACAM | CVAM | |
| | Control | | 2.37 | 2.58 | 0.54 | 3.84 | 0.04 | 0.13 | 7 |
| | Control | | 1.88 | 2.28 | 0.38 | 5.38 | 0.17 | 0.00 | 8 |
| | Control | | 2.06 | 2.06 | 0.19 | 4.60 | 0.12 | 0.00 | 7 |
| −7 | $ZnCl_2$ | 1.10 | 7.01 | 8.50 | 1.04 | 10.4 | 0.59 | 0.40 | 21 |
| −7 | $CoCl_2$ | 1.16 | 5.53 | 8.01 | 0.67 | 8.12 | 0.22 | 0.20 | 17 |
| −7 | $CaCl_2$ | 1.35 | 3.24 | 4.25 | 0.49 | 8.32 | 0.35 | 0.16 | 13 |
| +10 | $BaCO_3$ | 0.76 | 4.77 | 5.67 | 0.50 | 8.40 | 0.28 | 0.21 | 15 |
| −7 | $PdCl_2$ | 0.85 | 4.26 | 5.97 | 0.71 | 11.0 | 0.36 | 0.29 | 17 |
| −7 | $SnCl_2/H_2O$ | 0.66 | 3.55 | 4.19 | 0.39 | 6.31 | 0.21 | 0.15 | 11 |
| −7 | $MnCl_2/2H_2O$ | 0.93 | 8.21 | 10.7 | 1.17 | 14.5 | 0.43 | 0.42 | 27 |
| −7 | $Cp_2TiCl_2$ | 0.60 | 8.92 | 11.7 | 1.68 | 13.9 | 0.30 | 0.22 | 28 |
| −11 | $Yb(O_3SCF_3)_3$ | 0.24 | 5.65 | 8.52 | 0.77 | 12.3 | 0.23 | 0.20 | 21 |
| +4 | $Sn(O_2C(C_6H_{12})CH_3)_2$ | 0.37 | 1.44 | 2.00 | 0.20 | 4.33 | 0.00 | 0.00 | 6 |
| +18 | $La(OiC_3H_7)_3$ | 0.47 | 1.33 | 1.31 | 0.10 | 3.29 | 0.00 | 0.00 | 5 |
| −7 | $MnCl_2$ | 1.19 | 8.48 | 11.9 | 1.33 | 11.8 | 0.31 | 0.21 | 26 |
| −7 | $TiCl_4/2THF$ | 0.45 | 10.2 | 13.0 | 2.12 | 13.3 | 0.27 | 0.25 | 30 |
| −7 | $WCl_6$ | 0.38 | 7.17 | 9.58 | 1.09 | 14.2 | 0.39 | 0.27 | 25 |
| −7 | $Cp_2ZrCl_2$ | 0.51 | 8.03 | 12.1 | 1.31 | 13.7 | 0.32 | 0.25 | 27 |
| +9 | $Zr(C_5H_7O_2)_4$ | 0.31 | 3.47 | 3.74 | 1.16 | 5.77 | 0.14 | 0.20 | 11 |

TABLE 1-continued

| *pKa of HA | Catalyst Precursor | mmoles catalyst | monomers (mmoles) | | | | | | total monomers YIELD (%) |
|---|---|---|---|---|---|---|---|---|---|
| | | | HMD | 6ACN | ADN | CL | ACAM | CVAM | |
| −7 | (Cp$_2$ZrCl)$_2$O | 0.28 | 3.61 | 4.86 | 0.52 | 8.99 | 0.25 | 0.15 | 14 |
| +9 | V(C$_5$H$_7$O$_2$)$_3$ | 0.43 | 2.23 | 3.20 | 0.52 | 3.05 | 0.00 | 0.00 | 7 |
| −7 | Cp$_2$MoCl$_2$ | 0.51 | 7.31 | 9.61 | 1.03 | 13.93 | 0.54 | 0.41 | 25 |
| −7 | ReCl$_5$ | 0.41 | 7.03 | 8.57 | 0.81 | 13.07 | 0.42 | 0.30 | 23 |
| −7 | FeCl$_3$ | 0.92 | 8.47 | 11.50 | 1.17 | 13.03 | 0.36 | 0.22 | 26 |
| +35 | Ti(NMe$_2$)$_4$ | 0.67 | 3.00 | 3.04 | 0.35 | 5.05 | 0.14 | 0.12 | 9 |
| +18 | Ti(OiC$_3$H$_7$)$_4$ | 0.53 | 6.33 | 6.92 | 1.33 | 6.41 | 0.26 | 0.28 | 16 |
| −10 | TiI$_4$ | 0.27 | 12.71 | 18.04 | 3.72 | 15.62 | 0.52 | 0.56 | 39 |
| −10 | ZnI$_2$ | 0.47 | 6.98 | 11.62 | 1.03 | 9.45 | 0.28 | 0.15 | 22 |
| −8 | TiBr$_4$ | 0.41 | 7.73 | 9.36 | 0.92 | 11.76 | 0.34 | 0.21 | 23 |
| −7 | K$_2$PtCl$_4$ | 0.36 | 6.53 | 9.45 | 1.23 | 13.22 | 0.41 | 0.44 | 24 |
| −7 | CrCl$_3$ | 0.95 | 8.07 | 10.81 | 1.33 | 12.78 | 0.45 | 0.31 | 25 |
| +4 | Cu(O$_2$CCH$_3$)$_2$ | 0.83 | 4.53 | 5.46 | 0.76 | 6.87 | 0.23 | 0.20 | 14 |
| +9 | Co(C$_5$H$_7$O$_2$)$_2$ | 0.59 | 2.71 | 3.73 | 0.45 | 4.71 | 0.12 | 0.13 | 9 |
| +4 | Mn(O$_2$CCH$_3$)$_2$ | 0.87 | 3.52 | 3.39 | 0.39 | 2.80 | 0.00 | 0.13 | 8 |
| +35 | TiO$_2$ | 1.88 | 2.46 | 4.08 | 0.51 | 4.49 | 0.20 | 0.14 | 9 |
| +18 | Zr(OC$_3$H$_7$)$_4$ | 0.46 | 3.11 | 4.10 | 0.43 | 7.27 | 0.29 | 0.22 | 12 |
| +9 | TiO(C$_5$H$_7$O$_2$)$_2$ | 0.58 | 5.24 | 8.56 | 1.63 | 4.87 | 0.19 | 0.15 | 16 |
| +4 | Zn(O$_2$CCH$_3$)$_2$ | 0.82 | 2.40 | 3.50 | 0.48 | 3.61 | 0.00 | 0.00 | 8 |
| +3 | ZnF$_2$ | 1.45 | 4.74 | 6.53 | 0.69 | 5.98 | 0.16 | 0.17 | 14 |
| +35 | Ga$_2$O$_3$ | 0.80 | 2.81 | 3.25 | 0.23 | 5.84 | 0.24 | 0.00 | 9 |
| −11 | Yb(O$_3$SCF$_3$)$_3$ | 0.24 | 2.52 | 5.84 | 0.37 | 5.48 | 0.21 | 0.21 | 11 |
| −7 | NiCl$_2$/6H$_2$O | 0.63 | 5.05 | 6.13 | 0.45 | 11.40 | 0.35 | 0.22 | 18 |
| +9 | Zn(C$_5$H$_7$O$_2$)$_2$ | 0.57 | 0.99 | 1.55 | 0.18 | 1.98 | 0.00 | 0.00 | 4 |
| −7 | CuCl | 0.79 | 9.51 | 14.88 | 1.17 | 14.68 | 0.36 | 0.35 | 31 |
| −7 | CuCl$_2$ | 1.12 | 6.90 | 8.75 | 0.70 | 12.56 | 0.39 | 0.24 | 22 |
| −11 | CuI | 0.79 | 12.22 | 20.11 | 3.00 | 16.00 | 0.47 | 0.50 | 39 |
| −8 | CuBr | 1.05 | 5.59 | 10.54 | 0.84 | 8.56 | 0.22 | 0.14 | 20 |
| −7 | AlCl$_3$ | 1.13 | 12.35 | 18.53 | 2.80 | 17.19 | 0.38 | 0.39 | 39 |
| +2 | ZnSO$_4$ | 0.93 | 3.83 | 5.15 | 0.58 | 7.74 | 0.21 | 0.15 | 13 |
| −11 | Zn(O$_3$SCF$_3$)$_2$ | 0.41 | 5.15 | 7.45 | 0.58 | 8.45 | 0.20 | 0.00 | 17 |
| −7 | ScCl$_3$ | 0.99 | 12.66 | 18.73 | 2.96 | 16.27 | 0.44 | 0.34 | 39 |
| −7 | YCl$_3$ | 0.77 | 4.73 | 8.72 | 0.54 | 6.55 | 0.00 | 0.00 | 15 |

*pKa's from "Advanced Organic Chemistry: Reactions, Mechanism, and Structure" By Jerry March (McGraw-Hill Book Co., N.Y., 1968) pg. 219–221

I claim:

1. A process for preparing a mixture of monomers comprising reacting a polyamide or mixture of polyamides with at least 1 equivalent of ammonia per amide group of the polymer at a temperature between 250° and 400° C. and at a pressure of at least 100 psig, characterized in that the reaction is carried out in the presence of a Lewis acid catalyst precursor and in the absence of hydrogen, wherein the Lewis Acid is a metal salt containing a cation selected from the elements listed in Group 2 of the Periodic Table, and at least one anion whose conjugate acid has a pKa<15.

2. A process for preparing a mixture of monomers comprising reacting a polyamide or mixture of polyamides with at least 1 equivalent of ammonia per amide group of the polymer at a temperature between 250° and 400° C. and at a pressure of at least 100 psig, characterized in that the reaction is carried out in the presence of a Lewis acid catalyst precursor and in the absence of hydrogen, wherein the Lewis Acid is a complex containing an element selected from scandium, titanium, yttrium, and zirconium, and at least one anion whose conjugate acid has a pKa<20.

3. A process for preparing a mixture of monomers comprising reacting a polyamide or mixture of polyamides with at least 1 equivalent of ammonia per amide group of the polymer at a temperature between 250° and 400° C. and at a pressure of at least 100 psig, characterized in that the reaction is carried out in the presence of a Lewis acid catalyst precursor and in the absence of hydrogen, wherein the Lewis Acid is a complex containing a metal selected from the metals listed in Groups 5–14 of the Periodic Table, and at least one anion whose conjugate acid has a pKa<4.

4. A process for preparing a mixture of monomers comprising reacting a polyamide or mixture of polyamides with at least 1 equivalent of ammonia per amide group of the polymer at a temperature between 250° and 400° C. and at a pressure of at least 100 psig, characterized in that the reaction is carried out in the presence of a Lewis acid catalyst precursor and in the absence of hydrogen, wherein the Lewis Acid is a complex containing a cation selected from the group consisting of scandium, titanium, manganese, rhenium, iron, copper, zinc, molybdenum, tungsten, and aluminum, and at least one anion selected from the group consisting of chlorine, bromine, and iodine.

5. The process of claim 4, wherein the Lewis Acid precursor is a complex selected from the group consisting of ScX$_3$ TiX$_4$, MnX$_2$, ReX$_5$, FeX$_3$, CuX$_2$, CuX, ZnX$_2$, MoX$_6$, WX$_6$, and AlX$_3$, where X=Cl, Br, or I.

6. The process of claims 1, 2, 3, 4, or 5, wherein the polyamides to be reacted are selected from the group consisting of polyhexamethylene adipamide (nylon 6,6), polycaproamide (nylon 6), and mixtures thereof; and the monomers obtained from the reaction of said polyamides are selected from the group consisting of hexamethylenediamine, 5-cyanovaleramide, adiponitrile, caprolactam, 6-aminocaproamide, and 6-aminocapronitrile.

* * * * *